United States Patent [19]

Grubhofer

US005773011A

[11] Patent Number: 5,773,011
[45] Date of Patent: Jun. 30, 1998

[54] METHOD OF PREPARING A SYNERGISTIC IMMUNOLOGICAL ADJUVANT FORMULATION

[75] Inventor: Nikolaus Grubhofer, Gaiberg, Germany

[73] Assignee: Gerbu Biotechnik GmbH, Gaiberg, Germany

[21] Appl. No.: 505,409

[22] Filed: Jul. 21, 1995

Related U.S. Application Data

[63] Continuation-in-part of Ser. No. 153,406, Nov. 16, 1993, abandoned.

[30]     Foreign Application Priority Data

Sep. 27, 1993  [DE]  Germany ........................... 43 32 825.3
Sep. 30, 1993  [DE]  Germany ........................... 43 33 376.1

[51] Int. Cl.$^6$ ..................... A61K 45/00; A61K 31/30; A01N 59/06; A01N 55/02
[52] U.S. Cl. ..................... 424/278.1; 424/614; 424/724; 424/719; 424/600; 424/622; 424/630; 424/689; 514/494; 514/499
[58] Field of Search ..................... 514/494, 499; 424/614, 724, 719, 600, 622, 689, 630

[56]     References Cited

U.S. PATENT DOCUMENTS

| 4,036,953 | 7/1977 | Adam et al. . |
| 4,094,971 | 6/1978 | Chedid et al. . |
| 4,395,399 | 7/1983 | Ovchinnikov et al. . |
| 4,578,269 | 3/1986 | Merein . |
| 4,801,578 | 1/1989 | Monsigny et al. . |
| 4,845,042 | 7/1989 | Newman et al. . |
| 4,877,612 | 10/1989 | Berger et al. . |
| 5,109,026 | 4/1992 | Hoskinson et al. . |
| 5,376,369 | 12/1994 | Allison et al. . |
| 5,409,698 | 4/1995 | Anderson et al. . |

FOREIGN PATENT DOCUMENTS

| 646378 | 4/1995 | European Pat. Off. . |
| 9400153 | 1/1994 | WIPO . |

OTHER PUBLICATIONS

Byars, Noelene E., et al. (1987) "Adjuvant formulation for use in vaccines to elicit both cell–mediated and humor immunity ", Vaccine, 5:223–228.
Grubhofer, N. (1995) "An adjuvant formulation based on N–acetylglucosaminyl–N–acetylmu- ramyl–L–alanyl–D–isoglutamine with dimethyldioctadecy- lammonium chloride and zinc–L–proline complex as syn- ergists ", Immunology Letters, 44:19–24.
Vogel, F.R., et al. (1995) "A Compendium of Vaccine Adjuvants and Excipients ", in: Vaccine Design, M.F. Powell & M.J. Newman Eds. Plenum publishing Corp NY in press.
Hilgers et al, Cellular Immunol. 90:14–23, 1985.
Hilgers et al, Cellular Immunol. 86:393–401, 1984.
Hilgers et al, Cellular Immunol, 92:203–209, 1985
Hilgers et al, Int. Archs. Allerg. Appl. Immunol. 79:388–391, 1986.
Woodard et al. Inf & Imm. 30 (2): 409–412, 1980.
Arakawa et al 1993. Adv. Drug Delivery Rev. 10 : 1–28.
Flosdorf et al 1935. J. Immumol. 29 : 389–425.
Hilgers et al 1986 Int. Archs. Allergy Appl Immunol 79 : 392–96.
Nesmeyanov et al. 1990 Biomedical Science 1(2) : 151–154.
Abeshira–Amer et al 1987 Mol. Immunol 24(9):945–51.
Nash et al, 1985. J. Reprod. Immunol. 7:151–162.
Sharma et al, 1988 Tech. Adv. in Vacc. Dev. pp 107–116.
Shimizu et al 1992. Int. Immunopharm. 14(8):1415–20.
Audibert et al, 1977, Ann. Immunol 128C: 653–61.
Andronova et al, 1991. Sov. Med. Rev. D. Immunol. 4: 1–63.
Auci et al 1993, Int. Arch. Allergy Immunol, 101: 167–176.
Khullar et al, 1988. Immunol Invest. 17(1): 1–17.
Ott et al, 1995. In: Vaccine Design: The subunit and Adju- vant Approach Ed.
Powell et al. Plenum Press NY pp. 277–295 Bomford 1992. Med. Virol. 2:169–174.
Carelli et al. 1981, Inf & Imm. 33(1) : 312–314.
Alam et al, 1991 Immunol Lett. 27: 53–58.
Teerlink et al, 1987, Vaccine 5 :307–314.
Edelman et al, 1990, Intern. Rev. Immunol.7:51–66.
Grubhofer et al 1993. In: Animal Cell Technology: Basic&Applied Aspects, vol. 5:557–564. Eds: Kaminogawa et al.
Hilgers et al, 1992. Res. Immunol, 143:494–503.
Grubhofer et al, 1994, FASEBJ. 8(4–5): A993.
Allison et al 1988 Tech. Adv. Vacc. Dev. pp. 401–409.
Bennett et al, 1992. J. Immunol Methods. 153:31–40.
Tsujimoto et al, 1986, Inf&Imm. 53(3) : 511–516.
Allison et al, 1986, J. Immunol, Methods, 95:157–168.
Gregeriadis et al 1989. Immunol Lett. 20:237–240.
Yin et al 1989. J. Biological Resp. Modifiers 8:190–205.
Esher et al, 1974, J. Nat'l Cancer Institute 53(1):209–212.
Desowitz et al, et al, 1980. Inf & Imm. 27(1): 87–89.
Wong et al, 1976, Int. Arch Allergy Appl. Imm. 50:155–163.
Dzata et al, 1991, Vet. Microbiol, 29:15–26.
Audibert et al, 1984, Inf. Imm. 45(1):261–66.
Richards et al, 1988, Inf. & Imm. 56(3):682–686.
Warren et al, 1986, Ann. Rev. Immunol. 4:369–88.
Stanfield et al 1973. The Lancet 3 Feb 1973 pp. 215–219.

Primary Examiner—Nita Minnifield
Attorney, Agent, or Firm—Townsend and Townsend and Crew LLP

[57]     ABSTRACT

The improved method uses N-acetylmuramyl-L-alanyl-D-isoglutamine (MDP) or N-acetylglucosaminyl-N-acetyl-muramyl-L-alanyl-D-isoglutamine (GMDP) in low dose ranges in a combination with zinc-L-proline complex and with immunostimulating lipid in doses which synergistically potentiate the effect of each single component whereby the zinc-L-proline complex contains an excess of L-proline or 5-oxo-L-proline which serves as a solubiliser and dispersing agent for the lipid component.

20 Claims, 1 Drawing Sheet

METHOD OF PREPARING A SYNERGISTIC IMMUNOLOGICAL ADJUVANT FORMULATION

This application is a continuation-in-part application of U.S. patent application Ser. No. 08/153,406, filed Nov. 16, 1993, (now abandoned) which claims priority to German patent application P 43 32 825.3, filed Sep. 27, 1993 and German patent application P 43 33 376.1, filed Sep. 30, 1993.

The present invention relates to immunological techniques and, more specifically to the art of enhancing the natural immune response in animals and humans by combining the injected antigens with improved adjuvant formulations.

BACKGROUND OF THE INVENTION

If proteins or infectious material, called antigens, enter the humoral system of an animal or a human, an immune response occurs which culminates in the formation of antibodies. In many cases the antibody levels generated in the blood are too low for protecting animals or humans against disease, for use in the manufacture of commercial vaccines and for preparing antibodies in scientific research.

Finding methods that assist an organism to make more antibodies is therefore a field of endeavour which has been active for over a century.

DESCRIPTION OF PRIOR ART

Adjuvants for human use consist almost exclusively of a suspension of aluminium hydroxide, a polycationic, insoluble, protein adsorbing colloid.

Adjuvants for use with animals have frequently been developed by building on the very important contribution made by Jules Freund almost half a century ago. Jules Freund namely introduced an adjuvant formulation useful with animals consisting of a cream-like emulsion of a mineral oil (paraffin), synergistically combined with bacterial cell walls from dead mycobacteria such as *M. tuberculosis*. This became widely known and used as Freund's complete adjuvant (FCA). It is capable of elevating the antibody concentrations in the blood by several orders of magnitude over the natural" response with merely aqueous solutions of the antigen. For a comprehensive review see J. Freund, "The mode of Action of Immunologic Adjuvants" in Advances of Tuberculosis Research 7, 130–48 (1956). Freund's adjuvant is still commonly used in spite of severe drawbacks. The injected mineral oil can, namely, cause heavy and unsightly granulomas leading to the loss of animals. The bacterial material also contributes to undesirable side effects such as fever, granulomas, inflammations and arthritic symptoms [H. S. Warren & L. A. Chedid (1988) CRC Critical Reviews in Immunology 8, 83–101]. It is these effects which give rise to ethical reservations against the use of this adjuvant.

Many efforts have been made to emulate Freund's adjuvant in its efficacy and at the same time to avoid the damage evoked by this agent. In the intensive search for a replacement of the bacterial components (*Mycobacterium tuberculosis* or *M. butyricum*) it was found that low molecular weight glycopeptide subunits of the bacterial cell wall were about as effective as the native bacteria when applied in the same way as the parent mycobacteria, namely along with oil emulsions. N-acetylmuramyl-L-alanyl-D-isoglutamine (MDP) was the first of the compounds described. [F. Ellouz, A. Adam, R. Ciorbaru & E. Lederer (1974) Biochem. Biophys. Res. Commun 59, 1317–25]. More recently a glucosamine homolog of MDP, the N-acetylglucosaminyl-N-acetylmuramyl-L-alanyl-D-isoglutamine (GMDP), has been isolated from *Lactobacillus bulgaricus* and an efficient method of synthesis has been developed which makes this compound generally accessible. [V. Ivanov & T. Andronova (1991) Sovjet Medical Reviews, D. Immunology 4, 1–63 (R. V. Petrov, ed.), Harwood Academic Publishers; USSR Pat 2,543,268; U.S. Pat. No. 4,395,399]. GMDP has found considerable interest as a tumor inhibiting substance and has undergone extensive clinical and toxicological testing for this application.

Thus the cell wall of the mycobacteria that are used in Freund's adjuvant contain glycopeptide subunits such as N-acetylmuramyl-L-alanyl-D-isoglutamine (MDP) and N-acetylglucosaminyl-N-acetylmuramyl-L-alanyl-D-isoglutamine (GMDP), These subunits, i.e. MDP and GMDP, as well as a large number of chemically modified analogs and derivatives, have been investigated for use as adjuvants.

A study of the immunostimulating effect of MDP leads to the statement that 'MDP in saline does not induce DTH' (delayed time hypersensitivity, an indication for immunoresponse) to antigens. [Carelli, F. M. Audibert & L. A. Chedid (1981) Infection and Immunity 33, 312–14; Likewise, a lysozymic, cell-wall lysate containing MDP and GMDP amongst others was found to yield no significant increase in antibody count. [L. A. Chedid & F. M. Audibert, U.S. Pat. No. 4,094,971] and it has been demonstrated that doses of 100 μm per mouse given in aqueous solution are inactive.

It has been reported that in even more elevated doses (e.g. 500 μg/mouse) MDP acts as an immune suppressor. [C. Leclerc, D. Juy, E. Bourgeois & L. Chedid (1979) Cellular Immunology 45, 199–206].

The use of lipophilic MDP analogs to augment the levels antibody to β-human chorion gonadotropin in rabbits has been studied. Strong local lesions were reported. In doses of 250 μg per rabbit, combined with peanut oil emulsions, antibody yields were obtained, 2,5–7 times higher than those achieved with antigen in water alone. Unmodified MDP was less effective. No comparison was made with Freund's adjuvant [H. A. Nash, C. C. Chang & Y. Y. Tsong, (1985) J. of Reproductive Immunology 7, 151–62].

A study of the adjuvant effect of stearoyl-MDP found that it did not significantly stimulate antibody production, but that it did prime the animals so that when they were boosted two months later, an antibody response was seen which was about 0.3 that produced by Freund's adjuvant. Underivatised MDP in water was not used. [P. Sharma et al. (1988) Technological Advances in Vaccine Development, 107, 107–16, Alan Liss Publishers].

An adjuvant formulation consisting of a threonine analog of MDP in an oil emulsion carrier has been described which is presumably more biocompatible than Freund's adjuvant formulation. [A. C. Allison & N. E. Byars (1986) Journal of Immunological Methods 95, 157–68; A. C. Allison & N. E. Byars (1988) Technological Advances in Vaccine Development, 401–9, Alan Liss publishers; The antibody response however is considerably lower than with Freund's adjuvant [J. S. Kenney, B. W. Hughes, M. P. Masada & A. C. Allison (1989) Journal of Immunological Methods 121, 157–66].

The majority of the cited research has concentrated on the use of adjuvant formulations which are related to Freund's formula, consisting of relatively massive doses of thick oil emulsions, and containing MDP or its modifications at doses equivalent to the mycobacteria doses used in Freund's formulations.

The consensus is therefore [R. Bomford, (1992) Reviews in Medical Virology 2, 169–74] that as adjuvants they only work together with oil emulsions and in the doses which are similar to the ones which are deemed necessary for the mycobacteria in Freund's adjuvant, and that only chemical modification of the native glycopeptides will make better immunoadjuvants out of them.

FURTHER TECHNOLOGICAL BACKGROUND NOT BELONGING TO THE PRIOR ART

My copending U.S. patent application Ser. No. 08/130,645, corresponding to German patent number 4 231 675 describes work concerned with the use of MDP and GMPD to achieve improved immunoresponse without severe side effects. I have demonstrated that the doses of MDP and GMDP that were used in the cited research and in many other studies were, surprisingly, much too high to be optimally useful. Improved stimulation was shown to occur at doses 100 times lower. Moreover, it was discovered that at these lower doses the oil emulsion was not necessary and that simple aqueous solutions worked just as well or better. The extremely important discovery that simple aqueous solutions can be used is particularly important with regard to the avoidance of side effects.

When going to larger animals the low optimum doses of MDP and GMDP were confirmed, however the absolute antibody yields could not compete with those obtained with Freund's adjuvant, as shown in Table 2. The effect of those glycoppeptides must therefore be improved by some means to be of practical use as components of an adjuvant formulation in livestock and humans.

OBJECTS OF THE INVENTION

It is a first object of the present invention to provide new adjuvant formulations containing MDP and/or GMDP and other components as well as new methods for the use that dramatically enhance the safety, convenience and effectiveness of the glycopeptides as immunostimulants.

A further object of the invention is to achieve a synergistic interaction of the components which rapidly yields high antibody titers without boosting by repeated injections. This object is particularly important where one single injection is most desirable such as in the vaccination of humans and pets. Another object of the invention is to provide adjuvant formulations for veterinary and human medicines which are novel and oil-free and which consist of immunostimulants of very low oral and parenteral toxicity which are applied in low doses, whereby the clinical and industrial safety data of said ingredients are already well established, thus facilitating approval of such formulations for veterinary and human use.

BEST MODE FOR CARRYING OUT THE INVENTION

The invention is based on immunisation experiments performed mainly with rabbits using bovine serum albumin as antigen, and it is centered on the concept of the synergism of two or three different immunomodulators with the notion that true synergism should be a potentiating and not merely an additive effect. Confirmatory tests have been run with other species and antigens in order to examine biocompatibility and to establish more efficient immunisation routines.

In my researches I recognised a guideline for the search of synergists in the fact that GMDP has been found to disappear from an organism very rapidly, being completely metabolised after only eight hours. This short life span is sufficient to trigger the release of various immunostimulating factors such as interleukins and macrophage stimulating polypeptides which influence the events in the immune response. I concluded that enzymes must play a crucial role in all these processes. I decided to focus my attention on substances which could function as coenzymes.

The trace elements copper, manganese, zinc, cobalt and selenium were incorporated in this study. The most pronounced adjuvant effect was found with zinc, and a lesser effect with copper and selenium. Manganese and cobalt had negligible effects.

Furthermore, as already mentioned, the efficiency of Freund's adjuvant also depends on the cream-like oil emulsion prepared from the lipid "Bayol F" or more recently from "Marcol 52", a paraffine fraction essentially consisting of n-dodecane. By a mechanism not yet well understood the parafin oil acts as an immunoadjuvant.

D. Gall (1966) Immunology 11, 669–86 has investigated a considerable number of lipidic substances, mostly amines with varying chain length, from primary to quaternary and has found dimethyl dioctadecyl ammonium bromide (DDA) among the most active ones. In the following two decades DDA has found widespread interest for its potential as an immunoadjuvant and even was applied in humans (cf. Stanfield, Gall, D. & Bracke, P. M. (1973) Lancet 1973, 215–19). However DDA has the same disadvantages as Freund's paraffin oil: it is not biodegradable and therefore upon injection makes long-lasting granulomas (aking nods) and it is cumbersome to use because like paraffin oil it must be sonicated or otherwise homogenized to be distributed in the solution of the antigen. Despite this drawback I decided to first investigate DDA as a model substance and as will be explained in the following found a new way of incorporataing it which overcomes this disadvantage.

The most important result, and the actual core of the present invention, is the finding that the combination of glycopeptides with zinc in the form of an aminoacid complex and with a lipid substance under proper conditions and dosage are able to provoke antibody titers that far exceed the mere additive affect of each individual component and also that of Freund's adjuvant.

Another important aspect is the ease of use of the adjuvant formulation by presenting it as a sterile, solid substance obtained by coevaporating the components from an ethanol solution in the presence of a large excess of amino acids both soluble in ethanol and water, such as L-proline or 5-oxo-L-proline. Upon reconstitution with the aqueous antigen solution, the lipid as a homogenous mixture with the amino acids forms a submicroscopically fine dispersion which readily associates with the protein, thus circumventing the need of input of mechanical energy to form an emulsion with all its disadvantages.

Another aspect is the biocompatibility of the new adjuvant formula achieved by using only minute quantities of the individual components. In the case of Freund's adjuvant one customarily uses 0.5 ml of paraffin oil per rabbit. In the present invention one usses 20 $\mu$l lipid per rabbit, i.e. 25000 times less! Without the need to use an emulsion it is possible, with the present invention, to give intravenous adjuvanted immunisations. By frequent repetition of adjuvanted antigen injections, a technique made possible because of the good biocompatibility and the low doses required in the method according to this invention, antibody titers could be reached that were hitherto considered to be unattainable so rapidly and intensely. An analog of DDA was tested which instead of the dioctadecyl residues contained the stearoylhydroxyethyl groups attached to the quaternary nitrogen (Hoe 4243 from Farbwerke Hoechst, 2× recrystallised from ethyl acetate. This is the biodegradable analog of DDA, a so-called esterquat.

Another lipid quaternary ammonium compound was highly purified injectable grade lecithin. The overall immunostimulatory effect was lower than with DDA but is offset by the tremendous advantage that lecithin is a pharmaceutical material suitable and already licenced for parenteral use in other human applications.

DESCRIPTION OF THE PREFERRED EMBODIMENTS

Figure 1:
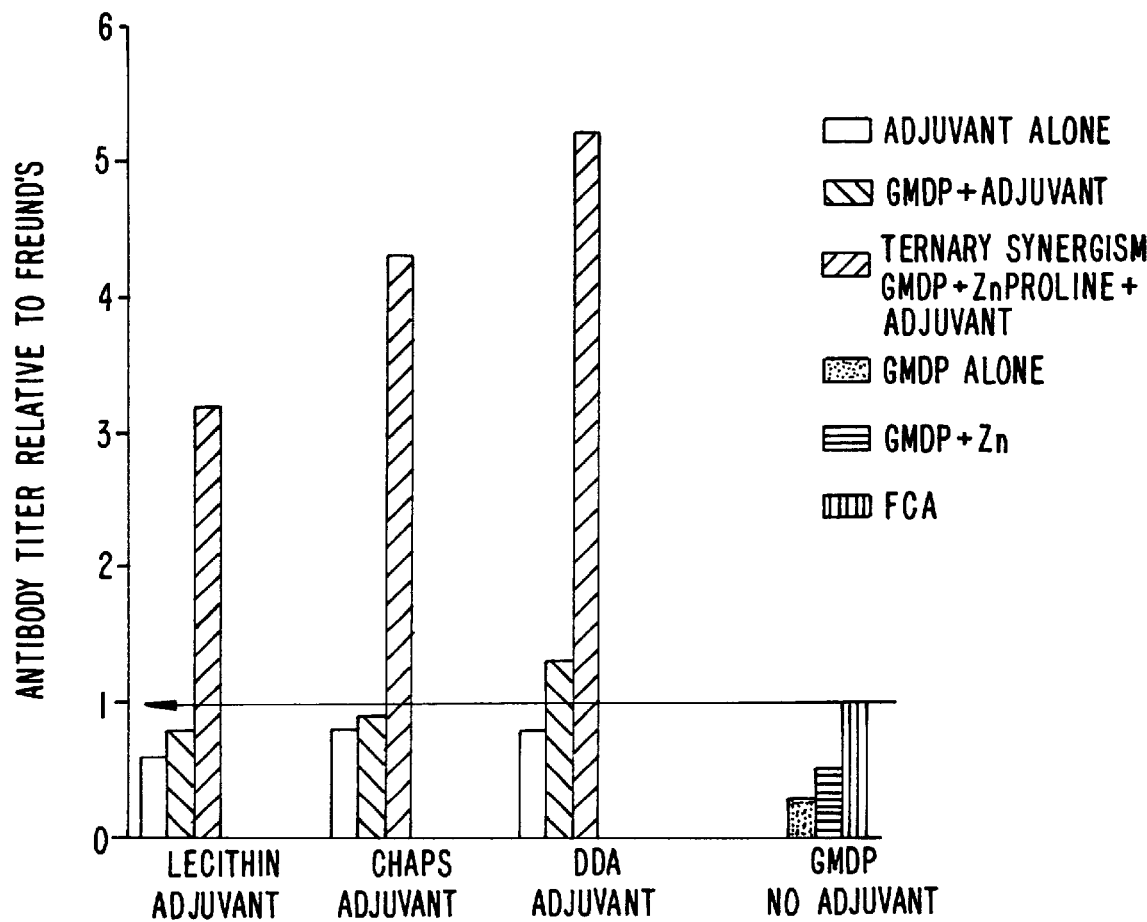
FIG. 1 is a diagram which illustrates the present invention.

In the work which led to the invention described in U.S. patent application Ser. No. 08/130,645 and in the corresponding German patent 42 331 675, it was established that the optimum dose of GMDP, for a rabbit is 10 μg. It has now been found that to date the optimum immunological adjuvant formulation for one injection for a rabbit comprises the combination of 10 μg GMDP+20 μg DDA+100 μg Zn as a complex with 1,4 mg L-proline for one rabbit injection (Experiment 18 of Table 1). This has been confirmed in a large number of rabbit experiments. The optimum dose of 10 μg GMDP per rabbit has been reconfirmed regardless of the nature of the supplementing synergists. There is indication however, that larger doses of DDA are required with antigens other than BSA and with larger species.

The zinc-L-proline complex was chosen because of the low toxicity of zinc-amino acid complexes as compared to simple salts, because of the high proline content of the new complex (apparently 8 mol proline to 1 atom zinc, but maybe $ZnPro_2$ solubilised in excess proline) which provides excellent dispersing action of this complex for the DDA which is virtually insoluble in water. The L-proline complex is moreover, as I have found, soluble in alcohol so that it can be coevaporated with the lipid and excess proline to form the solid body of the adjuvant formulation ready for reconstitution with aqueous antigen solution. In the case of lipids insoluble in 65% ethanol such as the Esterquat and cholesteryl stearate, the proline is replaced by 5-oxo-L-proline (pyroglutamic acid) which is well soluble in absolute ethanol. In thiscase the lipid can be dissolved in ethyl acetate and will not precipitate upon addition of the ethanol solution of the 5-oxoproline prior to the coevaporation.

A number of other combinations of immunostimulators have also been investigated, some with good success such as CHAPS, a steroid lipid with a strongly hydrophilic zwitterionic site that might be useful with vey sparesely soluble antigens, or cholestyeryl stearate and α-tocopherol as examples for neutral immunostimulating lipids. However, the potential that becomes available by combining glycopeptides in the right proportion and composition with synergists such as claimed is nearly inexhaustible. The present invention opens the door to further progress in synergistic adjuvant combinations.

EXAMPLE 1

In extended tests with rabbits, the temporal evolution of the anti-BSA titer under the influence of immunostimulants has been investigated and part of the results are shown in Table 1.

In this Table "A relative 28" signifies the antibody titer with adjuvants divided by the antibody titer with Freund's adjuvant after 28 days. The relative antibody titers quoted show three different values for each experiment, namely the A relative 28 values after 28 days, after 42 days and after 56 days, in each case relative to the value with Freund's adjuvant after 28 days. The $A_{rel}28$ data of day 42 in the experiments 1,3,6–14 and 21 are used in the drawing of FIG. 1. The progress obtained by the present invention is thus illustrated in this drawing which reflects the results shown in Table 1 below. The synergistic action of the individual components in three different adjuvant formulations is clearly demonstrated.

TABLE 1

The time course of the anti-BSA titer in rabbits with various adjuvant formulations

| Expt Nr | Component of Adjuvant Formulation | | | $A_{rel}28$ | | |
|---|---|---|---|---|---|---|
| | Glycopeptide | Amino acid complex | Adjuvant/lipid | Day 28 | Day 42* | Day 56 |
| 1* | 10 μg GMDP | | | 0.1 | 0.3 | 0.7 |
| 2 | 10 μg GMDP + | 10 μg Zn + 150 μg Pro | | 0.5 | 0.9 | 1.1 |
| 3* | 10 μg GMDP + | 100 μg Zn + 1.5 mg Pro | | 0.3 | 0.5 | 1.1 |
| 4 | 10 μg GMDP + | 10 μg Cu + 150 μg Pro | | 0.4 | 0.9 | 0.8 |
| 5 | 10 μg GMDP + | 100 μg Zn + 10 μg Cu + | 1.7 mg Pro | 0.5 | 1.2 | 1.1 |
| 6* | | | 10 μg Lecithin | 0.3 | 0.6 | 0.8 |
| 7* | | | 20 μg CHAPS | 0.5 | 0.8 | 0.9 |
| 8* | | | 20 μg DDA | 0.7 | 1.8 | 0.9 |
| 9* | 10 μg GMDP + | | 10 μg Lecithin | 0.7 | 1.0 | 1.1 |
| 10* | 10 μg GMDP + | | 20 μg CHAPS | 0.8 | 0.9 | 1.0 |
| 11* | 10 μg GMDP + | | 20 μg DDA | 1.0 | 1.3 | 1.2 |
| 12* | 10 μg GMDP + | 100 μg Zn + 1.5 mg Pro | 10 μg Lecithin | 0.8 | 3.2 | 3.5 |
| 13* | 10 μg GMDP + | 100 μg Zn + 1.5 mg Pro | 20 μg CHAPS | 1.5 | 4.3 | 4.4 |
| 14* | 10 μg GMDP + | 100 μg Zn + 1.5 mg Pro | 20 μg DDA | 1.3 | 5.2 | 4.3 |
| 15 | 10 μg MDP + | 100 μg Zn + 1.5 mg Pro | 20 μg DDA | 1.1 | 2.9 | 3.1 |
| 16 | 10 μg GMDP + | 100 μg Zn + 1.5 mg Pro | 20 μg Hoe 4243 esterquat | 1.0 | 4.4 | 5.2 |
| 17 | 10 μg GMDP + | 100 μg Zn + 1.5 mg Pro | 20 μg Cholesteryl stearate | 1.1 | 4.3 | 4.8 |
| 18 | 30 μg GMDP + | 100 μg Zn + 1.5 mg Pro | 20 μg DDA | 1.3 | 5.4 | 5.8 |
| 19 | 10 μg GMDP + | 100 μg Zn + 1.5 mg Pro | 20 μg α-Tocopherol | 0.7 | 2.9 | 2.9 |
| 20 | 10 μg GMDP + | 100 μg Zn + 1.5 mg Pro | 100 μg Dextrane 40 000 | 0.8 | 1.0 | 1.1 |
| 21* | Freund's Complete Adjuvant | | | 1.00 | 0.8 | 1.8 |

It is noted that the zinc proline complex used is that described in Examples 3 (or in Example 4 when using DDA as the lipid), prepared using zinc oxide of pharmaceutical quality, and that when the amino acid complex is an amino acid complex of copper the copper is used in the form of copper carbonate in the place of the zinc oxide. formation of the amino acid complex.

It is now interesting to analyse the information presented in Table 1. Experiment No. 21 gives the antibody titer for rabbits injected with Freund's complete adjuvant after 28 days, 42 days and 56 days. This titer is defined as 1 at 28 days and the relative value at day 42 is found to 0.8, i.e. a reduction relative to the value of 28 days but after 56 days the relative antibody titer has arisen to 1.8

Experiment 1 relates to the use of the optimum dose of GMDP on its own as established from my research and as claimed in the abovementioned U.S. patent application Ser. No. 07/130,645. It will be seen that with 10 $\mu$g of GMDP alone the relative antibody titer is 0.1 at day 28, 0.3 at day 42 and 0.7 at day 56. Although the 0.7 value at day 56 is still noticibly below the result obtained by Freund's complete adjuvant it is still a substantial improvement because the animals are not subjected to any particular stress and the mortality rate of the animals is substantially reduced. Experiments 2 to 5 show the results of using the same dose of GMDP with different amounts of divalent metals (in the form of zinc and/or Cu together with L-proline. It will be noted that using these adjuvant formulations better results are obtained than when using GMDP alone, with the best result being the 1.2 value of experiment 5 obtained using 10 $\mu$g of GMDP plus 100 $\mu$g of zinc plus 10 $\mu$g of copper plus 1.7 mg of L-proline. This value is already notably higher than the comparative value using Freund's adjuvant and is also particularly favourable because the mortality rate of the rabbits has significantly reduced and the rabbits are not subjected to the side effects and inherently stress which arises when using Freund's complete adjuvant.

Experiments 6, 7 and 8 show the effect of lecithin, CHAPS and DDA respectively when used alone as an adjuvant. When compared with the previous experiments these results are quite respectable, in particular the result of experiment No. 8 using 20 $\mu$g of DDA shows a favourable antibody titer of 1.8 at day 42 which compares very favourably with the value obtained with Freund's complete adjuvant.

Experiments 9, 10 and 11 show the antibody titers which are achieved when using using 10 $\mu$g of GMDP in combination with lecithin CHAPS and DDA. It will be seen that the combination of GMDP with lecithin and CHAPS results in slightly improved values over the use of lecithin and CHAPS alone. The combination of GMDP and DDA leads to improvement of the relative antibody titers at days 28 and 56, when compared to lecithin alone, but the value at day 42 is not so favourable as for DDA alone.

Particularly interesting are now the values for the relative antibody titers which are achieved with the experiments 12, 13 and 14 which clearly establish the synergistic effect underlying the present invention. Thus experiment 12 shows the combination of 10 $\mu$g of GMDP as glycopeptide plus 100 $\mu$g of zinc in the form of the zinc proline complex with 1.5 $\mu$g of proline in combination with 10 $\mu$g of lecithin. It is noted that the relative antibody titers at days 26, 42 and 56 of 0.8, 3.2 and 3.5 respectively are substantially higher than with a combination of 10 $\mu$g of GMDP and 10 $\mu$g of lecithin alone, at least with respect to titers at days 42 and 56. The values of 3.2 and 3.5 for days 42 and 56 are substantially better than with Freund's complete adjuvant, are surprisingly high and are obtained without the problematic side effects associated with Freund's complete adjuvant and without any unusual increase in animal mortality.

Since the substances involved can all be considered for human use there is a reasonable prospect that the same adjuvant could be used for human beings and that a substantial boost in a immune response will be achieved here.

The same general comments apply to the combination of 10 $\mu$g of GMDP with 100 $\mu$g of zinc in the form of zinc proline with 1.5 mg of proline and 20 $\mu$g CHAPS as used in experiment 13, and also for the similar formulation used for experiment 14 with the CHAPS substituted by DDA. Here it will be noted that at day 28 there is already a very significant increase over the antibody titer obtained with Freund's complete adjuvant and the values at 42 and 56 days are massively higher than the values obtained with Freund's adjuvant. Again formulations of this kind could be entertained for human use and the commercial value of such combinations and commercial products for use with animals is beyond dispute.

Experiment 15 corresponds closely to experiment 14 but uses 10 $\mu$g of MDP instead of 10 $\mu$g of GMDP. Although the results with MDP are not quite as good as with GMDP, they are still very respectable when compared with Freund's complete adjuvant and again do not result in the unwanted side effects or increased mortality rate associated with the use of Freund's complete adjuvant.

Experiments 16 and 17 involve the use of two other lipid substances in the same dose as was used for the CHAPS and DDA of experiments 13 and 14, i.e. 20 $\mu$g. It will be noted that the results obtained with 20 $\mu$g Hoe 4243 esterquat of experiment 16 and of cholesteryl stearate of experiment 17 also result in extremely high relative antibody titers after 42 and 56 days.

Experiment 18 resembles experiment 14 but involves three times the dose of GMDP which also results in a slightly higher value at 42 and a better value at day 56, however GMDP is relatively expensive and the benefit gained by adding GMDP is outweighed by the cost consideration. Thus 10 $\mu$g GMDP is still considered to be the ideal dose for a rabbit.

Experiments 19 and 20 use two further substances in the form of $\alpha$-tocopherol (which is a lipid) and dextrane (a sugar) in place of the lipid substances used in experiments 12 to 14, $\alpha$-tocopherol is clearly useful but not as efficient as any of lecithin, CHAPS or DDA. Dextrane is also feasible but does not produce much improvement over Freund's complete adjuvant, although it does not have undesired side effects and higher mortality rates associated with Freund's complete adjuvant.

In any event the experiments 12 and 19 clearly show the synertistic effect of the three-part adjuvant formulation of the present invention comprising a glycopeptide, an aminoacid complex of a divalent biological trace metal and a lipid substance, and, when compared with the relevant experiments of 1 to 11, show that the three-part formulation is substantially better than the results obtained using just one or two of the components.

Thus Table 1 clearly shows that two different glycopeptides (GMDP and MDP) in combination with a proline compound of a divalent metal and any one of at least six different lipid substances leads to a synergistic effect and a substantially enhanced immune response.

Experimental:

The following are the experimental conditions for determining the temporal evolution of the antibody titers with the various immunostimulants.

Animals:

Rabbits inbred b+Kap Immunological Institute of the Latvian Academy of Science Wilnius. One experiment uses four animals.

Antigen:

100 µg bovine serum albumin (BSA) per injection. Adjuvanted antigen solution: The solution to be injected is prepared by injecting 1 ml of antigen solution into the vial with the dry adjuvant containing 100 µg GMDP plus the synergists in proportion and dispersing the solid in the antigen solution. The resulting liquid is turbid from finely dispersed DDA.

Injection:

100 µl of the antigen+adjuvant solution are injected into the hind flank of the rabbit at one single site by subcutaneous route.

Serum Collection:

Heparinised plasma was collected by ear vein bleeding. Antibody determination: Anti BSA-IgG titers were measured using a microplate sandwich ELISA assay for antibody to BSA. 96 well flat bottom microtiter plates were coated with 100 µl BSA coating solution (4 µg/ml) in a humid chamber over night at 4° C. Plates were then washed with phosphate buffered saline (PBS) and blocked with 200 µl PBS-gelatine blocking solution for 1 hour at 37° C. followed by three washes with PBS. Dilutions from serum 1/10–1/100 000 were added to the washed plates in 100 µg aliquots. Plates were incubated at 37° C. for two hours. Plates were washed three times and 100 µl peroxide in citrate buffer pH 5) was added for 15 minutes at room temperature. 100 µl of 2,5M phosphoric acid stop solution was added and the light absorbance at 450 nm was read using a microplate reader. Titers were calculated from raw absorbance data within the linear range using a linear regression program present in the plate reading machine. The reciprocal dilution of serum which shows a colour of 0.75 was defined at the "titer".

EXAMPLE 2

As part of the efforts to find the most efficient immunisation routine, a number of immunisations were done with rabbits, mice and hens as test animals using BSA, DNP-BSA and human lambda light chain /HILC) as antigens in order to check the general adjuvant effect of GMDP and synergists. A more efficient immunisation routine was applied here, consisting in more frequent adjuvanted antigen injections (multiple boosting) that was possible because of the good biotolerance of the new adjuvants and which lead to significantly higher antibody yields.

TABLE 2

Relative Antibody Titer $A_{rel}28$ various Animals and Antigens

| | Antigen $A_{rel}28$ | | | |
|---|---|---|---|---|
| Animal | BSA | DNP-BSA | Human LC | Human IgG |
| Rabbit | 10.8 | 7.6 | 8.9 | |
| Hen | 3.7 | 4.2 | 5.0 | 2.2 |
| Mouse | 3.7 | 4.2 | 5.0 | |
| Hamster | | | | 1.4 |
| Goat | | | | 0.3 |

Relative Antibody titers are the titers obtained with adjuvants as described under experimental, divided by the antibody titers with Freund's adjuvant after 28 days with the same animal under the experimental conditions described below.

Table 2 thus shows the enhanced immune response achieved by the present invention is not restricted to just one antigen in the form of BSA but rather also applies to three further antigens, namely DNP-BSA, human λ light chain and human IgG.

These results thus make it clear that the method and formulation of the invention is applicable to a variaty of animal species and to a variety of antigens. Experience with immune response using other adjuvant formulations permits the clear conclusion that the results presented here are strongly indicative that the same immune response will be obtained with other antigens and using other lipids and other lipids in the adjuvant formulation. Moreover, the research we have conducted indicates that proline compounds in general can be used in the adjuvant formulation in addition to the zinc L-proline and L5 oxoproline.

Experimental conditions for the results of Table 2:

Rabbits:

Groups of three. BSA 100 µg, DNP-BSA 50 µg, HILC 20 µg. Adjuvant formulation 10 µg GMDP, 20 µg DDA, 100 µg Zn. Immunise/boost: day 0.7, 14, 21, bleed at day 28

Hens:

Group of five. BSA 50 µg, DNP-BSA 20 µg, HILC 10 µg. Adjuvant formulation 5 µg GMDP, 10 µg DDA, 50 µg Zn 0.7 mg proline. Immunise/boost: day 0, day 21. Pool eggs from day 26–30. Important: subcutaneous route is much superior to i/m route. The IgY contained in the yolk of the eggs was enriched for ELISA test by the method of J. Wallmann, C. Staak & E. Luge (1990) J.Vet. Med. B37, 317–20.

Mice:

Group of five. BSA 20 µg, DNP-BSA 10 µg, HILC 10 µg. Adjuvant formulation 1 µg GMDP, 4 µg DDA, 10 µg Zn 150 µg proline. Immunise/boost: day 0, day 14, bleed at day 28. Blood was collected by tail vein bleeding. Animals were anaesthetisised prior to blood collection using metofane.

Hamsters:

Group of five. Human IgG 100 µg,. Adjuvant formulation 2 µg GMDP, 4 µg DDA, 20 µg Zn 300 µg proline. Immunise/boost: day 0, 14, 28, bleed day.

Goats:

Group of two. 200 µg Human IgG. Adjuvant formulation 300 µg GMDP, 3 mg zinc 450 mg proline, 20 mg ESTERQUAT Hoe 3242. Immunise/boost: day 0, 14, 28, bleed day 35.

ELISA testing as described sub Example 1. The results listed in Table 2 show that the efficiency of the new adjuvant formulation is a phenomenon that apparently is not limited to one particular animal species and to one single antigen. A further indication of this fact is that the individual components of the claimed adjuvant formulation have been observed to function as immunostimulants in a great variety of antigens, animals and experimental conditions at correspondingly lower levels.

EXAMPLE 3

Preparation of Zinc-L-proline Stock Solution

Into a 500 ml beaker on a magnetic hot plate place magnetic stirrer, 2.07 g Zinc oxide DAB 6 and 25.36 g L-proline DAB 6 (1:9 molecular ratio) and 200 ml 65% ethanol. Heat to gentle boiling under stirring. After a few minutes the ZnO has dissolved. Allow the solution to cool, transfer into a 250 ml volumetric flask and fill to the mark with 65% ethanol. Filter into a bottle for storage. 150 µl of this stock solution contain 1 mg zinc and 16.1 mg L-proline.

EXAMPLE 4

Preparation of the zinc-L-proline complex. 5 ml of the Zn-L-proline stock solution is diluted with isopropanol and cooled to +4° C. Large crystals form over night which are collected and washed with isopropanol, recrystallised from 65% EtOH-isopropanol and dried. The material is evidently zinc-L-proline salt [Cotton, F. A. & Hanson, H. P. (1959) J. Chem. Physics 28. 83–6] found; % C 42.23 H 5,76 N 9,40 Zn (as ZnO residue) 23.90. Calculated for $Zn.Pro_2$; $C_{10}H_{16}N_2O_2Zn$ % C 45.94 H 6,17 N 10.71 Zn 24.94. The excess L-proline apparently serves to solubilise the material in ethanol.

EXAMPLE 5

Adjuvant Formulation, Standard Dose DDA

When preparing the zinc L-proline solution per Example 3, put 167 mg GMDP (produced by Peptech Ltd., Cirencester U.K. unter U.S. Pat. No. 4,395,399, USSR Priority Nov. 2nd 1977) and 333 mg DDA (dimethyldioctadecylammonium chloride, GenaminSC) produced by Farbwerke Höchst AG recristallized from acetone) into the volumetric flask before adding the zinc-proline solution.

150 $\mu$l of this stock solution contains 100 $\mu$g GMDP, 200$\mu$ DDA, 1 mg zinc and 16.1 mg L-proline. Before dispensing the solution into the individual vials it is passed through a 0.2 $\mu$m-Poretics polycarbonate membrane filter. A standard volume of this solution is 150 $\mu$l to give a solid deposit containing 100 $\mu$g GMDP. If only a few vials are required for experiments a desiccator with sulfuric acid will dry the contents within some hours. For production of larger numbers of vials a vacuum dryer with 5 mbar and 37° C. temperature is suitable. The residue is a white substance which readily dissolves in the antigen solution to a slightly turbid dispersion.

EXAMPLE 6

Adjuvant formulation with very lipophilic compound. Into the vial is first pipetted 200 $\mu$l water containing 4 mg of the water soluble zinc L-proline salt ($ZnPro_2$) and lyophilized in place. After this, a solution containing 100 $\mu$g GMDP, 15 $\mu$g L-5 oxoproline (pyroglutamic acid) in 200 $\mu$l isopropanol+20 $\mu$g cholesteryl stearate in 100 $\mu$l ethyl acetate, total 300 $\mu$l of a clear solution is pipetted into the same vial which is then placed in the vacuum dryer at 30° C. and evacuated to 5 mbar, maintained for 3 hours. The residue readily dissolves in 1 ml water to slightly turbid solution, no particles can be seen in the microscope at 1:1000.

EXAMPLE 7

Dosage of ADJUVANT

Convenient portions of solid ADJUVANT for practical use in immunisations are 100 $\mu$g GMDP or 10 $\mu$g GMDP and corresponding synergists in a serum vial suitable for 10 immunisations of rabbits or mice respectively, obtained by pipetting 100 $\mu$l of ADJUVANT solution prepared according to example 6 into vials and drying them over sulfuric acid, experimental lots in a desiccator, production lots in a specially designed drying chamber.

EXAMPLE 8

Immunisation experiments with ADJUVANT

The purpose of these experiments was to establish faster immunisation routes by multiple boosting and to check the biotolerance of the ADJUVANT (10 $\mu$g GMDP, 20 $\mu$g DDA, 100 $\mu$g zinc+1,4 mg L-proline) with rabbits. The results are summarised in Table 3. The numerical data represent antibody titers expressed in reciprocal dilutions as described in Example 1.

No animal damage could be observed even with severely challenging daily doses of ADJUVANT. (cf. expt. 47). Antibody expression with very feeble antigen levels could be forced by daily immunisation with antigen and ADJUVANT (expt. 43,44). Adjuvant or GMDP alone injected separately from antigen is not effective (expt. 45–49).

TABLE 3

Efficiency and Tolerance Tests

| Expt. Nr. | 0 | 7 | 14 | 21 | 28 | 35 | 42 | Purpose of Experiment Comments |
|---|---|---|---|---|---|---|---|---|
| 33 | I | | | | I | | | Standard ADJUVANT check run |
| | — | | | | 4385 | | 26800 | d70: 32000, d84:12532 |
| 41 | I | | I | | I | | | Biweekly ADJUVANT check |
| | — | | 2440 | | 8324 | | 9273 | basis for all tests Table 3 |
| 42 | I | I | I | I | I | | | Weekly boosting 100 $\mu$g BSA |
| | — | 000 | 4376 | 20996 | 19460 | | 8976 | body temperature weight |
| 43 | i | i | i | i | i | | | Weekly boosting 25 $\mu$g BSA |
| | — | 000 | 140 | 228 | 88 | | | observe body temp DTH |
| 44 | iiiiiii | iiiiiii | iiiiiii | iiiiii | | | | Hyperboosting 25 $\mu$g BSA daily + |
| | — | 000 | 6379 | 18944 | 27136 | | 5440 | ADJUVANT body temperature ok |
| 45 | I aaaaaa | aaaaaa | I aaaaaa | aaaaaa I | | | | Imitation of an ADJUVANT depot |
| | — | | 1104 | | 8512 | | 8520 | compare with #41 |
| 46 | I gggggg | gggggg | I gggggg | gggggg I | | | | Imitation of pure GMDP depot |
| | — | | 28 | | 68 | | 156 | without synergists: inhibition |
| 47 | I AAAAAA | AAAAA | I AAAAA | AAAAA I | | | | Tolerance test with 10-fold dose |
| | — | | 420 | | 2244 | | | of ADJUVANT animals ok |
| 48 | BSA | | BSA | | BSA | | | Check the effect of ADJUVANT |
| | −a + 8 | | a − 8 | | a − 8 | | | injection 8 hours before the injection |
| | — | | 592 | | 184 | | 288 | of antigen 100 $\mu$g BSA |
| 49 | BSA | | BSA | | BSA | | | Check the effect of ADJUVANT |

TABLE 3-continued

Efficiency and Tolerance Tests

| Expt. Nr. | Events on given day, for explanation see footnotes | | | | | | Purpose of Experiment Comments |
|---|---|---|---|---|---|---|---|
| | 0 | 7 | 14 | 21 | 28 | 35 | 42 | |
| | −a + 1 | | a + 1 | | a + 1 | | | injection 1 hour after the injection |
| | — | | 34 | | 88 | | 324 | of antigen 100 μg BSA |
| 55 | FCA | | FCA | | FCA | | | Check standard routine with |
| | — | | 1028 | | 1796 | | 8964 | Freund's adjuvant |

Explanation of symbols for events in Table 3:
A   ADJUVANT reconstituted in water to 10 fold concentration (100 μg GMDP + synergists
a   ADJUVANT reconstituted in water standard concentration 100 μl injection
I   Immunize with ADJUVANT and 100 μg BSA
i   Immunize with ADJUVANT and 25 μg BSA
a − 8   Inject Adjuvant 8 hours prior to BSA of BSA
a + 1   inject ADJUVANT 100 μl 1 hour after injection
FCA   Immunize with 100 μg BSA + 100 μl Freund's complete adjuvant

I claim:

1. A method of forming an injectable medium comprising a synergistic immunological adjuvant formulation and an aqueous antigen solution, the method comprising the steps of:

mixing together a glycopeptide, an amino acid complex and a lipid substance finely dispersible or soluble in said amino acid complex, to form a homogeneous mixture, drying the homogeneous mixture whereby to obtain a fine dispersion of said lipid substance with the dried residue of said amino acid complex and said glycopeptide, and adding said aqueous antigen solution to said fine dispersion whereby said amino acid complex readily dissolves in water present in said aqueous antigen solution and said finely dispersed lipid substance combines with protein molecules forming said antigen and thus remains finely dispersed in said injectable medium.

2. Method as claimed in claim 1 wherein the lipid substance contains an amine group.

3. Method as claimed in claim 1 wherein the lipid substance contains a steroid residue.

4. Method as claimed in claim 1 wherein said lipid substance comprises a quaternary ammonium group.

5. Method as claimed in claim 1 wherein said lipid substance comprises a long-chain hydrocarbon group.

6. Method as claimed in claim 1 wherein said lipid substance comprises dimethyldioctadecylammonium bromide.

7. Method as claimed in claim 1 wherein said lipid substance is dimethyldioctadecylammonium chloride.

8. Method as claimed in claim 1, wherein the lipid substance is biodegradable.

9. Method as claimed in claim 8 wherein said lipid substance is dihydroxyethyl-dihydroxyethyl-stearoyl-ammonium chloride.

10. Method as claimed in claim 8 wherein said lipid substance is lecithin from eggs.

11. Method as claimed in claim 9 wherein said lipid substance is tocopherol.

12. Method as claimed in claim 10 wherein said lipid substance is cholesteryl stearate.

13. Method as claimed in claim 1 wherein said synergistic immunological adjuvant formulation comprises 1 part by weight of GMDP, 2 parts by weight of dimethyldioctadecylammonium bromide salt and 10 parts by weight of zinc contained in a complex with 140 parts by weight of L-proline.

14. Method as claimed in claim 1 wherein said synergistic immunological adjuvant formulation consists of 1 part by weight glycopeptide, 2 parts by weight of lipid, 10 parts by weight of zinc contained in a complex with 2 moles L-proline and 150 parts by weight of L-proline or 5-oxo-L-proline.

15. A method of forming an injectable medium comprising a synergistic immunological adjuvant formulation and an aqueous antigen solution, the method comprising the steps of:

mixing together GMDP, an amino acid complex and DDA to form a homogeneous mixture, drying the homogeneous mixture whereby to obtain a fine dispersion of DDA with the dried residue of said amino acid complex and said GMDP, and adding said aqueous antigen solution to said fine dispersion whereby said amino acid complex readily dissolves in water present in said aqueous antigen solution and said fine dispersion of DDA combines with protein molecules forming said antigen and remains finely dispersed in said injectable medium.

16. The method in accordance with claim 15, wherein said amino acid complex is a proline complex.

17. The method in accordance with claim 15, wherein said amino acid complex is a zinc proline complex.

18. A method of forming an injectable medium comprising a synergistic immunological adjuvant formulation and an aqueous antigen solution, the method comprising the steps of:

mixing together MDP, an amino acid complex and DDA to form a homogeneous mixture, drying the homogeneous mixture whereby to obtain a fine dispersion of DDA with the dried residue of said amino acid complex and said GMDP, and adding said aqueous antigen solution to said fine dispersion whereby said amino acid complex readily dissolves in water present in said aqueous antigen solution and said fine dispersion of DDA combines with protein molecules forming said antigen and remains finely dispersed in said injectable medium.

19. The method in accordance with claim 18, wherein said amino acid complex is a proline complex.

20. The method in accordance with claim 18, wherein said amino acid complex is a zinc proline complex.

* * * * *